United States Patent [19]
Rodgers et al.

[11] Patent Number: 5,459,222
[45] Date of Patent: Oct. 17, 1995

[54] UV-ABSORBING POLYURETHANES AND POLYESTERS

[75] Inventors: Juliana Rodgers, Staten Island; Istvan Borsody, Yonkers; Athanasios Karydas, New York; Robert A. Falk, New City; Karl F. Mueller, New York; Michele Kovaleski, Mahwah, all of N.Y.

[73] Assignee: Ciba-Geigy Corporation

[21] Appl. No.: 73,227

[22] Filed: Jun. 4, 1993

[51] Int. Cl.$^6$ .................................................. C08G 18/28
[52] U.S. Cl. ................................ 528/73; 528/74; 528/76; 528/85; 428/423.1; 428/423.4; 428/425.1; 560/24; 560/25; 560/26; 560/27; 560/32; 548/260; 548/261; 427/372.2; 427/387; 427/387.9; 427/391; 427/393
[58] Field of Search .................................. 528/73, 74, 85, 528/76; 428/423.1, 423.4, 425.1; 560/24, 25, 26, 27, 32; 548/260, 261; 427/372.2, 389, 389.9, 391, 393

[56] References Cited

U.S. PATENT DOCUMENTS

| | | | |
|---|---|---|---|
| 4,061,652 | 12/1977 | Schroeter | 260/308 |
| 4,179,548 | 12/1979 | Schroeter | 525/329 |
| 4,276,401 | 6/1981 | Karrer | 526/263 |
| 4,831,109 | 5/1989 | Mitra et al. | 528/73 |
| 4,845,180 | 7/1989 | Henry et al. | 528/73 |
| 4,853,471 | 8/1989 | Rody | 548/261 |
| 5,081,258 | 1/1992 | Kawaguchi | 548/260 |
| 5,274,016 | 12/1993 | Berrer et al. | 524/100 |

FOREIGN PATENT DOCUMENTS

| | | |
|---|---|---|
| 0010518 | 4/1980 | European Pat. Off. . |
| 0226538 | 6/1987 | European Pat. Off. . |
| 0342974 | 11/1989 | European Pat. Off. . |
| 2137935 | 10/1984 | United Kingdom . |

OTHER PUBLICATIONS

Encyclopedia of Polymer Science and Engineering; vol. 13, 1988, John Wiley & Sons; pp. 288–292.

*Primary Examiner*—James J. Siedleck
*Assistant Examiner*—R. F. Johnson
*Attorney, Agent, or Firm*—Kevin T. Mansfield; Michele A. Kovaleski

[57] ABSTRACT

Polyurethanes and polyesters are described which are the reaction products of an aromatic, aliphatic or cycloaliphatic diisocyanate, or of a diacid or diacid derivative respectively, with a diol containing a pendent UV-absorbing moiety, optionally also with one or more other diols or diamines. These UV-absorbing polycondensates can be applied to the surfaces of substrates by exhaustion methods or by spraying and act to protect polymers and dyes from degradation by UV radiation. They are therefore useful, either alone or in combination with other coating materials, for the treatment of wood, paper, textiles, leather or other surfaces which are exposed to degrading radiation.

13 Claims, No Drawings

UV-ABSORBING POLYURETHANES AND POLYESTERS

BACKGROUND AND PRIOR ART

The present invention relates to protecting porous surfaces from UV degradation. More particularly it relates to novel polymeric compounds useful for this purpose, to intermediates used in their preparation and to methods of applying compositions containing the polymers to porous substrates.

Ultraviolet radiation-absorbing compounds are almost universally present in polymers used in out-door applications. Typically they are molecules of medium molecular weight with specific UV-absorbing moieties, such as benzotriazoles, and are incorporated into the bulk of thermoplastics or rubbers during compounding, extrusion or molding steps. Often they are combined with radical-scavenging molecules, like hindered mines (HALS - hindered amine light stabilizers) or phenols.

UV absorbers can also be formulated into polymer coating systems in order to protect a substrate, but in this case their effectiveness is greatly influenced by the physical nature of the substrate. If the substrate is a hard surface, such as glass, metal or certain finished wood products, conventional UV stabilizers work quite well in protecting the coating in which they are applied and the underlying substrate. On porous substrates however, such as leather, paper or raw wood, their effectiveness is almost entirely lost because most of the active material diffuses below the surface of the substrate.

SUMMARY OF THE INVENTION

It has now been discovered that polyurethanes and polyesters of 1,000 to 15,000 molecular weight and containing at least 5 % and up to 80 % by weight of UV-absorbing moieties can provide excellent protection against fading of dyes or degradation of the substrate, even when this substrate is highly porous.

Bis-urethanes obtained by reaction of 2 equivalents of hydroxybenzotriazoles or benzophenones with 1 equivalent of a diisocyanate are described in U.S. Pat. Nos. 4,061,652 and 4,179,548; as phenol-derived urethanes, they are thermally unstable and reform the UV-absorbing molecule during heat curing.

Bis-ureas obtained from 2 equivalents of aminoalkyl-substituted hydroxybenzotriazoles and 1 equivalent of a diisocyanate are described in U.S. Pat. No. 5,081,258; here the essential doubling of the UV-absorbing molecule's molecular weight serves to make the additive less extractible, less prone to migration and eliminates the formation of colored complexes with iron or copper.

No polyurethanes containing more than two hydroxybenzotriazole or benzophenone units are described in the literature.

DETAILED DESCRIPTION

The polyurethanes of the present invention are of the general formula I

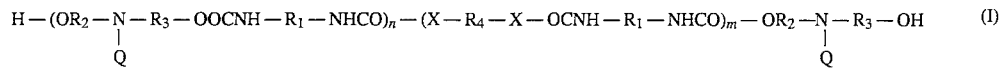

wherein
n is a number from 2 to 20,
m is zero to 5,
$R_1$ is the diradical residue of an aliphatic, cycloaliphatic or aromatic diisocyanate with structure OCN-$R_1$-NCO,
$R_2$ and $R_3$ independently of each other are $C_2$-$C_6$ alkylene,
$R_4$ is the diradical residue of a diol or diamine of 40 to 5000 molecular weight,
X is oxygen or -NH- and
Q is a radical of the formula

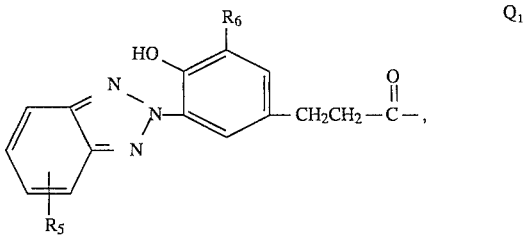

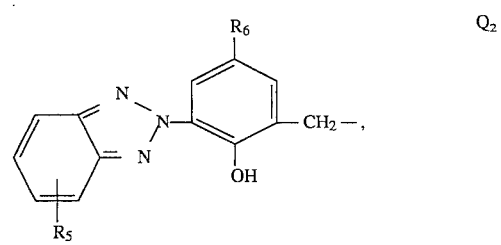

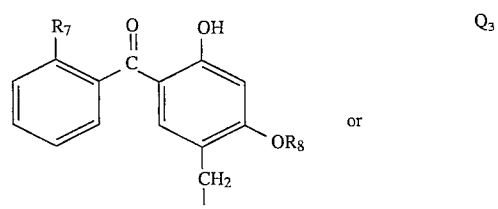

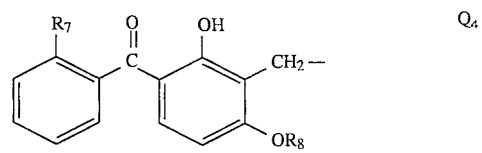

in which
$R_5$ is hydrogen, chlorine or $C_1$-$C_4$alkyl,
$R_6$ is $C_1$-$C_8$alkyl,
$R_7$ is hydrogen or hydroxyl and
$R_8$ is hydrogen or $C_1$-$C_8$alkyl,
with the proviso that the sum of m+n is such that the resulting polymer has an average molecular weight of 1,000 to 15,000.

The subscripts m and n refer to the average number of repeating units; a range of numbers and a corresponding distribution of molecular weights is actually obtained. The number average molecular weights of the polymers may be readily determined by gel permeation chromatography.

Diisocyanates of structure OCN-$R_1$-NCO useful in preparing polymers of the formula I include 1-isocyanatomethyl-5-isocyanato-1,3,3-trimethylcyclohexane (="isophorone diisocyanate"), hexane- 1,6-diisocyanate, 2,2,4-(2,4,4)-trimethylhexane- 1,6-diisocyanate, bis-(4-isocyanatocyclohexenyl)methane, ethylene diisocyanate, 1,2-diisocyanatopropane, 3-diisocyanatopropane, 1,2-diisocyanato-cyclohexane, 1,3-diisocyanatocyclohexane, 1,4-diisocyanatobenzene, bis(4-isocyanatocyclohexyl)methane, bis(4-isocyanatophenyl)-methane, 2,6- and 2,4-toluene diisocyanate, 3,3-dichloro-4,4'-diisocyanatobiphenyl, tris(4-isocyanatophenyl)methane, 1,5-diisocyanato-naphthalene, hydrogenated toluene diisocyanate, 1,3,5-tris( 6-isocyanato-hexyl)biuret, 2,2'-diisocyanatodiethyl fumarate, 1,5-diisocyanato-1-carboxypentane, 1,2-, 1,3-, 1,6-, 1,7-, 1,8-, 2,7- and 2,3-diisocyanatonaphthalene, 2,4- and 2,7-diisocyanato-1-methylnaphthalene, 4,4 '-diisocyanatobiphenyl, 4,4'-diisocyanato-3,3'-diisocyanato- 6(7)-methylnaphthalene, 4,4'-diisocyanato-2,2'-dimethylbiphenyl bis-(4-isocyanatophenyl)ethane and bis(4-isocyanatophenyl) ether. All are commercially available.

One preferred group of polymers of formula I are those wherein $R_1$ is the diradical residue of a diisocyanate of structure $OCN-R_1-NCO$ selected from the group above and m is zero.

Preferred diisocyanates of the structure $OCN-R_1-NCO$ include 1-isocyanato-methyl-5-isocyanato- 1,3,3-trimethyl-cyclohexane (="isophorone diisocyanate"), hexane- 1,6-diisocyanate, 2,2,4-(2,4,4)-trimethylhexane-1,6-diisocyanate and bis-(4-isocyanatocyclohexenyl)methane.

Preferred are polymers of formula I wherein
m is zero
n is 2 to 10,
$R_1$ is the diradical residue of a diisocyanate of structure $OCN-R_1-NCO$ selected from the group consisting of 1-isocyanatomethyl-5-isocyanato-1,3,3-trimethyl-cyclohexane, hexane-1,6-diisocyanate, 2,2,4-(2,4,4)-trimethylhexane-1,6-diisocyanate and bis-(4-isocyanatocyclohexenyl)methane,
$R_2$ and $R_3$ are ethylene,
Q is $Q_1$,
$R_5$ is hydrogen and
$R_6$ is tertiary butyl.

Also preferred are polymers of formula I wherein
m is zero
n is 2 to 10,
$R_1$ is the diradical residue of a diisocyanate of structure $OCN-R_1-NCO$ selected from the group consisting of 1-isocyanatomethyl-5-isocyanato-1,3,3-trimethylcyclohexane, hexane-1,6-diisocyanate, 2,2,4-(2,4,4)-trimethylhexane-1, 6diisocyanate and bis-(4-isocyanatocyclohexenyl)methane,
$R_2$ and $R_3$ are ethylene,
Q is $Q_2$,
$R_5$ is hydrogen and
$R_6$ is tertiary butyl.

Also preferred are polymers of formula I wherein
m is zero
n is 2 to 10,
$R_1$ is the diradical residue of a diisocyanate of structure $OCN-R_1-NCO$ selected from the group consisting of 1-isocyanatomethyl-5-isocyanato-1,3,3-trimethylcyclohexane, hexane-1,6-diisocyanate, 2,2,4-(2,4,4)-trimethylhexane-1, 6diisocyanate and bis-(4-isocyanatocyclohexenyl)methane,
$R_2$ and $R_3$ are ethylene,
Q is $Q_3$ or $Q_4$, $R_7$ is hydrogen and
$R_8$ is methyl.

Another preferred group of polymers of formula I are those wherein
m is 1 or more and
$R_4$ is the diradical residue of a poly-($C_2$-$C_4$alkyleneoxide), a poly-(dimethylsiloxane)-$\alpha$,$\omega$-dialkylene of 500 to 3000 molecular weight or a tertiary nitrogen-containing diol residue of 40 to 500 molecular weight.

Within this group, especially preferred are polymers of formula I wherein
m is greater than 1,
n is 2 to 5,
$R_1$ is the diradical residue of a diisocyanate of structure $OCN-R_1-NCO$ selected from the group consisting of 1-isocyanatomethyl-5-isocyanato- 1,3,3-trimethylcyclohexane, hexane-1,6-diisocyanate, 2,2,4-(2,4,4)-trimethylhexane-1,6-diisocyanate and bis-(4-isocyanatocyclohexenyl)methane,
$R_2$ and $R_3$ are ethylene,
Q is $Q_1$,
$R_4$ is a poly-(tetramethyleneoxide) or a tertiary nitrogen-containing diol residue of 40 to 500 molecular weight,
$R_5$ is hydrogen and
$R_6$ is tert-butyl.

Also preferred are polymers of formula I wherein
m is greater than 1,
n is 2 to 5,
$R_1$ is the diradical residue of a diisocyanate of structure $OCN-R_1-NCO$ selected from the group consisting of 1-isocyanatomethyl-5-isocyanato- 1,3,3-trimethylcyclohexane, hexane- 1,6-diisocyanate, 2,2,4-(2,4,4)-trimethylhexane-1,6-diisocyanate and bis-(4-isocyanatocyclohexenyl)methane,
$R_2$ and $R_3$ are ethylene,
Q is $Q_2$,
$R_4$ is a poly-(tetramethyleneoxide) or a tertiary nitrogen-containing diol residue of 40 to 500 molecular weight,
$R_5$ is hydrogen and
$R_6$ is tert-butyl.

Also preferred are polymers of formula I wherein
n is 2 to 5,
$R_1$ is the diradical residue of a diisocyanate of structure $OCN-R_1-NCO$ selected from the group consisting of 1-isocyanatomethyl-5-isocyanato-1,3,3-trimethylcyclohexane, hexane- 1,6-diisocyanate, 2,2,4-(2,4,4)-trimethylhexane-1,6-diisocyanate and bis-(4-isocyanatocyclohexenyl)methane,
$R_2$ and $R_3$ are ethylene,
Q is $Q_3$ or $Q_4$,
$R_4$ is a poly-(tetramethyleneoxide) or a tertiary nitrogen-containing diol residue of 40 to 500 molecular weight,
$R_7$ is hydrogen and
$R_8$ is methyl.

The polyesters of the present invention are of the general formula II

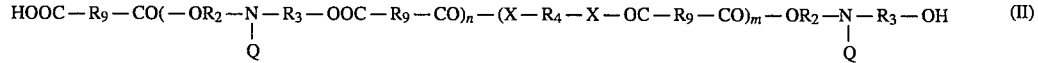

wherein
n is a number from 2 to 20, ,
m is zero to 5, $R_9$ is the diradical residue of an aliphatic, cycloaliphatic or aromatic di- or tetra-carboxylic acid with structure HOOC-$R_9$-COOH, $R_2$ and $R_3$ independently of each other are $C_2$-$C_6$alkylene, $R_4$ is the diradical residue of a diol or aliamine of 40 to 5000 molecular weight, X is oxygen or -NH- and Q is one of the structures $Q_1$, $Q_2$, $Q_3$, or $Q_4$ as described above, with the proviso that the sum of m+n is such that the resulting polymer has an average molecular weight of 1,000 to 15,000.

As with the polyurethanes, m and n refer to average values.

Preferred di- and tetracarboxylic acids HOOC-$R_9$-COOH, and reactive derivatives thereof for the preparation of polyesters of the formula II include succinic acid, maleic acid, itaconic acid and phthalic acid as well their corresponding arthydrides, acid chlorides and $C_1$-$C_4$-alkyl esters; glutaric and adipic acid, isophthalic and terephthalic acid and their corresponding acid chlorides and $C_1$-$C_4$-alkyl esters; also useful are dianhydrides like benzophenone-tetracarboxylic acid dianhydride and pyromellitic dianhydride.

Most preferably, $R_9$ is the diradical residue of succinic, maleic or adipic acid. Preferred dianhydrides are pyromellitic and benzophenone-tetracarboxylic acid dianhydrides.

Diols useful in preparing polymers of the formula I or II containing the UV-absorbing benzotriazole moiety $Q_1$ are of the structure IIIa:

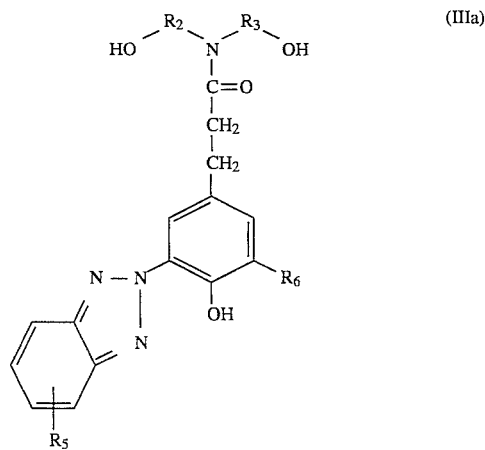

in which $R_2$, $R_3$, $R_4$, $R_5$ and $R_6$ are as described above. Such compounds are described in U.S. Pat. No. 4,853,471.

Diols with moieties $Q_2$ are of the structure IIIb:

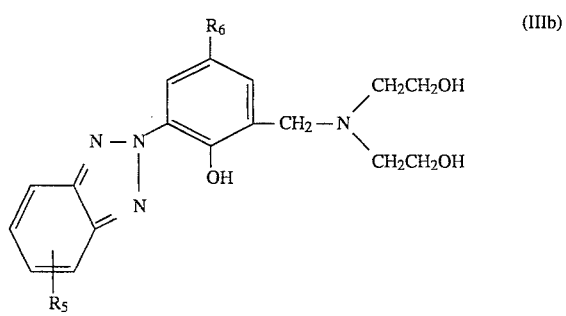

in which $R_5$ and $R_6$ are as described above.

Diols containing the benzophenone moieties $Q_3$ or $Q_4$ are of the formula IIIc or IIId:

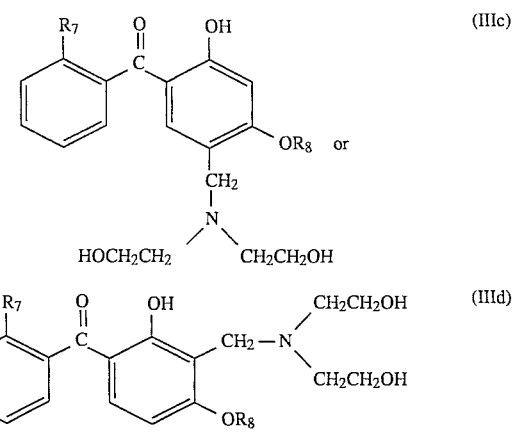

in which $R_7$ and $R_8$ are as described above.

The novel intermediates of formulae IIIb, IIIc and IIId are a further object of this invention.

Preferred chain-extending diols and diamines of the structure HX-$R_4$-XH include branched or linear $C_3$-$C_{10}$alkyl diols and diamines; tertiary nitrogen-containing diols of 40 to 500 molecular weight like N-methyl-diethanolamine, N-phenyl-diethanolamine, N-toloyl-diethanolamine, N,N'-dihydroxyethyl-piperazine, N,N'-dihydroxypropyl-piperazine, N-$C_2$-$C_{20}$-alkyl di(hydroxyethyl)- and di(hydroxypolyethoxyethyl)-amines; N-methyl-bis(3-aminopropyl)amine; ether-diols like diethyleneglycol and tetraethyleneglycol; di-secondary amines like N,N'-dimethyl-1,3-propanediamine; polyester-diols of 500 to 3000 molecular weight made from saturated or unsaturated dicarboxylic acids and $C_2$-$C_{10}$alkylene diols; poly-(alkyleneoxide) diols and diamines, wherein alkylene denotes a branched or linear alkylene group with 2–4 carbon atoms; or poly-(dimethylsiloxane)-α,ω-dialkanols or -dialkylene amines of 500 to 3000 molecular weight.

Typical chain-extending poly-($C_2$-$C_4$alkyleneoxide)-moieties are derived from poly-(ethyleneoxide)diol, poly-(propyleneoxide)diol, poly-(tetramethyleneoxide)diols, or poly-(ethyleneoxide)-α,ω-dialkyleneamine and poly-(tetramethyleneoxide)-α,ω-dialkyleneamines, or from ethyleneoxide-propyleneoxide block copolymer diols and diamines; chain-extending polysiloxanes are poly-(dimethylsiloxane)-α,ω-dialkanols, wherein the alkanol group is an aliphatic hydrocarbon group with 3 to 6 carbon atoms and poly-(dimethylsiloxane)-α,ω-dialkyleneamines, wherein the alkyl group is an aliphatic hydrocarbon group with 3 to 6 carbon atoms.

Synthesis

The first step in the synthesis of the inventive polyurethanes and polyesters consists in making the UV-absorbing diol precursor. A benzotriazole-diol of structure IIIa can be made, for instance, from a benzotriazole-ester by transamidification with a dialkanolamine as described in detail in the examples. The reaction can be carried out in bulk or, preferably, in a solvent. Useful solvents include toluene, xylene, high boiling ketones like methyl isobutyl ketone and ethers like ethyleneglycol dimethylether. Benzotriazole-diols of structure IIIb and benzophenone-diols of structure IIIc and IIId can be made by the Mannich reaction, that is aminoalkylation with formaldehyde and diethanolamine, as illustrated in the examples.

Polyurethanes of formula I are subsequently synthesized by reaction of a diol of the formula IIIa, IIIb, IIIc or IIId with a diisocyanate and, optionally, another chain-extending diol or diamine component, using known methods of polyurethane synthesis. The reaction is preferably carded out using a diluting solvent like 2-butanone, xylene, toluene, ethyleneglycol dimethylether, or a mixture thereof. Useful catalysts include dibutyltin dilaurate, stannous octoate, sodium methoxide or tertiary amines like triethylamine. If the polyurethane of formula I contains no water-solubilizing groups, its solution is then emulsified in water, using a nonionic, anionic or cationic surfactant or a mixture thereof, and the organic solvent is stripped off. The examples describe the process in detail. If the polyurethane contains a sufficient number of polyethylene oxide groups or tertiary amino groups, the polymer may be soluble or dispersible in water at neutral or acidic pH.

Suitable anionic surfactants can be either so-called water-soluble soaps or water-soluble synthetic surface-active ingredients.

Soaps are the alkali metal, alkaline earth metal or substituted or unsubstituted ammonium salts of higher fatty acids ($C_{10}$-$C_{22}$), for example the sodium or potassium salts of oleic or stearic acid, or of naturally occurring fatty acid mixtures, which can be obtained, for example, from coconut oil or tallow oil. The fatty acid methyltaurine salts may furthermore also be mentioned.

More often, however, so-called synthetic surfactants are used, in particular fatty alcohol sulfonates, fatty alcohol sulfates, sulfonated benzimidazole derivatives or alkylarylsulfonates.

The fatty alcohol sulfonates or sulfates are as a rule in the form of alkali metal, alkaline earth metal or substituted or unsubstituted ammonium salts and contain an alkyl radical having 8 to 22 C atoms, alkyl also including the alkyl moiety of acyl radicals, for example the sodium or calcium salt of ligninsulfonic acid, of dodecylsulfate or of a fatty alcohol sulfate mixture prepared from naturally occurring fatty acids. These also include the salts of sulfuric acid esters and sulfonic acids of fatty alcohol-ethylene oxide adducts. The sulfonated benzimidazole derivatives preferably contain 2 sulfonic acid groups and a fatty acid radical having 8–22 C atoms. Alkylarylsulfonates are, for example, the Na, Ca or triethanolamine salts of dodecylbenzenesulfonic acid, dibutylnaphthalenesulfonic acid or a naphthalenesulfonic acid-formaldehyde condensation product.

Corresponding phosphates, for example salts of the phosphoric acid ester of a p-nonylphenol-(4-14)-ethylene oxide adduct, or phospholipids are furthermore also suitable.

Nonionic surfactants are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols.

Other suitable nonionic surfactants are the water-soluble polyethylene oxide adducts containing 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit.

Examples of nonionic surfactants are nonylphenol polyethoxyethanols, castor oil polyglycol ether, polypropylene-polyethylene oxide adducts, tributylphenoxy-polyethoxyethanol, polyethylene glycol and octylphenoxypolyethoxyethanol.

Fatty acid esters of polyoxyethylenesorbitan, such as polyoxyethylenesorbitan trioleate, are furthermore also suitable.

The cationic surfactants are in particular quaternary ammonium salts which contain at least one alkyl radical having 8 to 22 C atoms as the N-substituent and lowerhalogenated or unhalogenated alkyl, benzyl or lower hydroxyalkyl radicals as further substituents. The salts are preferably in the form of halides, methylsulfates or ethylsulfates, for example stearyltrimethylammonium chloride or benzyldi(2-chloroethyl)ethylammonium bromide.

The optimum amount of surfactant to employ can be determined by routine experimentation.

These surfactants are described, inter alia, in the following publications:

"*McCutcheon's Detergents and Emulsifiers Annual*", MC Publishing Corp., Glen Rock, N.J., 1988.

M. and J. Ash, "*Encyclopedia of Surfactants*", Vol. I-III, Chemical Publishing Co., New York, 1980–1981.

Dr. Helmut Stache "*Tensid-Taschenbuch*" (Surfactant Handbook), Carler Hanser Verlag, The polyesters of formula II are synthesized by any of the known methods of polycondensation, for example by melt condensation from the UVA- diols with di-acids or anhydrides, by transesterification with the lower-alkyl esters of dicarboxylic acids or by reaction with diacid chlorides. If dianhydrides are used, the free carboxylic acid groups allow dispersability of the polymer at basic pH. Otherwise they may be dispersed using the same surfactants as the polyurethanes.

Application

The UV-absorbing polyurethanes and polyesters of the present invention, in the form of emulsions or solutions, can be applied to a substrate by various means. If the substrate is leather, the polymer can be applied by a batch exhaustion method, but preferably it is applied to one surface only by spraying. For textiles a padding operation can be used and for paper, addition to wet pulp; but here also, surface application by a spraying or a coating process is preferable. It is possible to mix the inventive UV-absorbing polymers with other finishing agents for paper, leather or textiles, especially filmforming polymers and oil and water repellent fluorochemical polymers. After application the substrate is dried, preferably at a temperature above 50° C.

The UV-absorbing polymers of the present invention can function to protect a substrate itself, or to protect dyes with which the substrate has been colored, or other finishes which have been applied to the substrate. Preferably the substrate is porous.

The following non-limiting examples illustrate various aspects of the invention. Examples 1 and 2 show the synthesis of benzotriazole-diols.

EXAMPLE 1

2-[Bis(2-hydroxyethyl)amino]carbonyl ethyl)phenyl]-benzotriazole.

2-[2 '-Hydroxy-3'-t-butyl-5'-(2-methoxycarbonyl ethyl)phenyl]-benzotriazole (BTZ) ( 1000 g, 2.83 mol) and diethanolamine (446. 18 g, 4.24 tool) are placed in a one-liter jacketed reactor equipped with nitrogen inlet and stirrer. The mixture is blanketed with nitrogen and heated until it melts into a black liquid, and then stirred at 130° C. The reaction's progress is monitored by gas chromatography and is complete after 8 hours. The reaction mixture is then cooled to 65° C. where it turns to a green-yellow solid mass. Two liters of methanol are added and the solid sample turns into a black slurry. The slurry is taken from the reactor and placed in a 4 liter beaker equipped with a mechanical stirrer.

The excess diethanolamine is removed by adding 140 g AMBERLYST-15 ion exchange resin (from Rohm and Haas Co.) and stirring for 15 minutes. The resin is removed by vacuum filtration. The removal of diethanolamine from the sample is monitored by gas chromatography. Finally the methanol is stripped off on a vacuum rotary evaporator and a light tan powder is isolated, which is 2-[bis(2-hydroxy ethyl)amino]carbonyl ethyl)phenyl]benzotriazole, or BTZ-diol of the formula IIIa. GC/MS indicate a purity of 94%, the remainder being unreacted starting material (BTZ). The equivalent weight of the product was found to be 228, compared to a theoretical value of 215.

EXAMPLE 2

2-(2-Hydroxy-3-(bis(2-hydroxyethyl)aminomethyl-5-methylphenyl)-2H-benzotriazole.

2-(2-Hydroxy-5-methylphenyl)-2H-benzotriazole (25.0 g, 0.11 mol), diethanolamine (17.5 g, 0.167 mol) and paraformaldehyde (5.7,0.189 mol) are dissolved in 37 ml of n-butanol. The mixture is heated with agitation at reflux (95 to 100° C) for 16 hours. Since thin layer chromatography (TLC) indicated the reaction was incomplete, it was heated an additional 24 hours at which time TLC indicated complete reaction. The solvent is then removed by vacuum distillation to give a viscous liquid product in high yield. This Mannich base is identified as the above-named compound by $^1$H-NMR.

EXAMPLE 3

3(5)-Diethanolaminomethyl-2-hydroxy-4-methoxy-benzophenone.

To a one liter 3-necked flask equipped with condenser, stirring shaft and dropping funnel fitted with a gas inlet tube are added 2-hydroxy-4-methoxybenzophenone (150.0 g, 0.66 mol), formaldehyde (116.3 g, 37.4 % solution in water) and 225 ml ethylene glycol dimethyl ether. Diethanolamine (139.0 g, 1.32 mol) is charged to the dropping funnel and dripped into the reaction vessel with agitation over a period of 10 minutes. Following this addition, the reaction mixture is heated to 80° C. and held at this temperature for 16 hours with stirring and introducing a stream of nitrogen gas. After this time, the formation of product is confirmed by thin layer chromatography, using toluene as the mobile phase. The mixture is cooled and poured into a 3-1 Erlenmeyer flask; 1.5 l water are added and the mixture is cooled in an ice bath. The product oils out and the water layer is decanted. The oil is washed once more with 200 ml of water. The oil is dissolved in toluene and the water-toluene azeotrope mixture is distilled off. The remaining solvent is removed in vacuo and 140 g (96% of theory) of the product is obtained in form of a viscous yellow liquid. $^1$H- NMR shows that the product is a mixture of compounds IIIc and IIId in molar ratios of approximately 1:1 (BPO-diol). The equivalent weight of the product was found to be 166 compared to a theoretical value of 173.

EXAMPLE 4

Synthesis of a BTZ-diol-polyurethane.

First 70 g (0.1535 mol) of the diol of Example 1 and 130 g of 2-butanone (MEK) are placed into a flask equipped with stirrer, nitrogen inlet and a thermo-regulator. The mixture is heated to 105° C. under nitrogen and approximately 20 % of the 2-butanone is distilled off to remove any water. The reaction mixture is then cooled to 80° C. and 22.03 g (0.134 mol) of hexamethylene diisocyanate (HDI) are added together with 0.42 g (0.00067 tool) of dibutyltin dilaurate and 32 g of 2-butanone. The reaction mixture is stirred at 80° C. for two hours, after which time the reaction is complete as determined by IR-spectroscopy.

The product is a 40% solution in MEK of a polyurethane containing the BTZ-diol of Example 1 and HDI in a molar ratio of 8:7.

EXAMPLE 5

Synthesis of a poly-ether/BTZ-diol co-polyurethane.

First 29.39 g (0.01527 tool) of poly-(butyleneoxide)glycol (POLYMEG 2000, from Quaker Oats Chemical Company) and 44.1 g of 2-butanone (MEK) are placed into a flask equipped with stirrer, nitrogen inlet and a thermo-regulator and heated to 80° C. Then 5.01 g (0.0306 mol) of hexamethylene diisocyanate (HDD are added along with 7.8 g of 2-butanone and 0.09 g (0.00014 tool) dibutyltin dilaurate. The mixture is stirred for 45 min. at 80° C. and is monitored by NCO titration. After the NCO-value has dropped to approximately one half of its original value—indicative of an isocyanate capped poly-(butyleneoxide) glycol prepolymer—2.5 g (0.0153 mole) of HDI are added along with 13.97 g (0.0305 tool) of the diol of Example 1. The mixture is heated for an hour following this addition, after which time the reaction is complete, as determined by IR-spectroscopy.

The product is a 40% solution in MEK of a polyurethane, containing the BTZ-diol of Example 1, poly-(butyleneoxide) glycol and HDI in mole ratios 2:1:3.

EXAMPLES 6–9

Following the procedure of Example 4, the polyurethanes listed in the following table are synthesized as 40% solutions in 2-butanone.

| Example Nr. | Mol Ratio BTZ-diol/HDI |
| --- | --- |
| 6 | 3/2 |
| 7 | 4/5 |
| 8 | 5/4 |
| 9 | 6/5. |

EXAMPLES 10–13

Example 8 is repeated using the diisocyanates listed below to make 40% solutions in MEK of polyurethanes containing the BTZ-diol of Example I and the diisocyanate in a mol ratio of 5/4.

| Example Nr. | Diisocyanate |
| --- | --- |
| 10 | isophorone diisocyanate, MW: 222 |
| 11 | 3,3,4(4,3,3)-trimethylhexane-1,6-diisocyanate, MW: 213 |
| 12 | DIMER ACID diisocyanate (General Mills Co.), MW: 594 |
| 13 | 4,4'-diisocyanato-diphenylmethane; MW: 258. |

EXAMPLE 14

Synthesis of a cationic BTZ-diol-co-polyurethane.

First 100 g (0.25 mol) of the BZT-diol of Example 1 and 30 g of toluene are added to a 1-liter jacketed reactor equipped with a nitrogen sparge, condenser and stirrer. The mixture is stirred at 110° C. until it becomes a clear amber liquid; then cooled to 72° C. and 120 g 2-butanone (MEK) are added. To the slightly hazy amber liquid 34.6 g (0.201 mol) of hexamethylene diisocyanate (HDI) are added along with 51.9 g of MEK and 0.27 g (0.015 mol) of dibutyltin dilaurate catalyst The mixture is stirred at 72° C. for 45 minutes; then 6.85 g (0.0575 mol) of N-methyldiethanolamine (NMDA) are added along with 10.3 g of 2-butanone and the mixture is kept at 60° C. for 15 minutes. The reaction is complete as determined by IR spectroscopy.

The product is a 40 % polyurethane solution in toluene and 2-butanone. It contains the BTZ-diol of Example 1, HDI and NMDA in a mol ratio of a 6:7:2.

Upon drying, a clear, hard, brown polymer is obtained which is dispersible in aqueous acetic acid solution.

EXAMPLE 15

First 100 g (0.25 mol) of the diol of Example 1,250 g of 2-butanone (MEK) and 30 g of xylene are placed into a flask equipped with a stirrer, nitrogen inlet and a thermo-regulator. The mixture is heated to reflux under nitrogen and, after dissolution of the diol, 64.9 g (0.375 mol) of hexamethylene diisocyanate (HDI) is added, followed by 22.35 g (0.187 moles) of N-methyldiethanolamine (NMDA). The mixture is kept at reflux for five hours, after which time no free isocyanate can be detected by IR.

The product is a 40% solution in MEK of a polyurethane containing the BTZ-diol of Example 1, HDI, and NMDA in a mol ratio of 1.3:2:1.

The polymer solution dries to a very hard, glossy, brown film, which is soluble in dilute acetic acid.

EXAMPLE 16

Synthesis of a BPO-diol-polyurethane.

First 60 g (0.181 mol)of the BPO-diol of Example 3 and 111 g of 2-butanone (MEK) are placed into a flask equipped with stirrer, nitrogen inlet and a thermo-regulator. The mixture is heated at 105° C. under nitrogen and approximately 20 % of the 2-butanone is distilled off to remove any water. The reaction mixture is then cooled to 80° C. and 27.32 g (0.158 mol) of hexamethylene diisocyanate (HDD are added together with 0.49 g of dibutyltin dilaurate and 41 g of 2-butanone. The reaction is stirred at 80° C. for two hours, after which time the reaction is complete as determined by IR-spectroscopy.

The product is a 40% MEK solution of a polyurethane containing the BPO-diol of Example 3 and HDI in a mole ratio of 8:7.

EXAMPLE 17

Emulsification of an inventive polyurethane.

First 200 g of the polyurethane solution of Example 4 (46.21% solids) is added to a 400 ml beaker along with 31 g of 2-butanone. The mixture is covered to prevent the loss of solvent and stirred and heated to 65° C. This phase is the organic phase and is a clear amber liquid.

Then to a 800 ml beaker are added 1.11 g of Ethomeen S/12® (bis(2-hydroxyethyl)soy amine) and 5.91 g of Arquad 2 C/75® (dimethyldicocoammonium chloride), both from Akzo Chem. Inc. Next 370 g distilled water are added with agitation. This mixture, the aqueous phase, is also heated to 65° C., forming a cloudy liquid.

When both phases have reached 65° C., the organic phase is added gradually to the aqueous phase while stirring, forming a hazy yellow liquid. After stirring for approximately one minute, the mixture is charged to the holding vessel of a Microfluidizer® from MICROFLUIDS® Corp. The sample is passed six times through this machine at 5000–6000 psi, during which time it turns into a milky white emulsion with a slight bluish tint. This emulsion is then placed into a single-neck flask and the 2-butanone is stripped off at 60° C. and 25 mm Hg vacuum on a vacuum rotary evaporator. The final solids content is 20%.

EXAMPLE 18

Using the same procedure, the polyurethane-polyether of Example 5 is emulsified to produce a 20% aqueous emulsion.

EXAMPLE 19

The BZT-diol of Example 1 is also emulsified, using the same emulsifiers and process steps as described in Example 17. This emulsion serves as a control for the application examples described below.

EXAMPLE 20

The following example demonstrates the superiority of the inventive polyurethane-bound BTZ UV-absorbers (UVAs) over the monomeric BTZ-diol UV-absorber.

The BTZ-UVA emulsions prepared according to Examples 17 and 18 are spray-applied to the surface of brown aniline leather to give an add-on of 1.17 g actives/ft$^2$. The sprayed leather is subsequently dried at 70° C. for ten minutes, put into exposure frames and then subjected to UV radiation in an Atlas xenon arc WEATHER-O-METER controlled irradiation exposure system for 48 hours. The results are shown in the following Table:

| Sample Emulsion of: | UVA (% of solid) | Fade resistance |
|---|---|---|
| Example 19 (BTZ-diol control) 40% actives/solids | 100 | little |
| Example 17 75% actives/solids | 75 | much improved |
| Example 18 25% actives/solids | 25 | much improved |

EXAMPLE 21

The following example shows the performance of the inventive BTZ-UV-absorbing polyurethanes in comparison to other low-MW UV-absorbers designed for aqueous applications.

The products are spray-applied to the same leather as above for an add-on of 0.54g/ft$^2$ actives, put into exposure frames and exposed to various kilo-joules (KJ) of radiation in the WEATHER-O-METER. The results are measured on a gray-scale according to AATCC Test Method 16-1990. In this test a rating of 5 denotes no noticeable fading; a rating of 1 the greatest degree of color change due to fading. The results are given in the following table.

| | Gray-Scale values after irradiation | | | |
|---|---|---|---|---|
| Product | 25 KJ | 75 KJ | 95 KJ | 150 KJ |
| CIBAFAST-W, a monomeric, water-soluble benzotriazole type UV-absorber | 2–3 | 2 | 1–2 | — |
| LS008, a monomeric experimental water-soluble benzotriazole type UV-absorber | 2 | 1–2 | 1 | — |
| Polymer emulsion of example 17 | 4–5; 5 | 3–4 | 3 | 2–3 |
| untreated control | — | 1–2 | — | 1 |

EXAMPLE 22

Synthesis of a UVA-absorbing polyester.

First 50 g (0.104 moles) of the benzotriazole-diol of Example 1 and 13.03 g (0.132 moles) of succinic anhydride are placed in a 250 ml reaction flask equipped with a stirrer, nitrogen inlet tube, reflux condenser with water separator and temperature controller. Then 30 g of toluene are added and the mixture is heated to reflux. The progress of the reaction is monitored both by GC and by the amount of water collected. After 17 hours 120 g of toluene are added, resulting in a polyester solution of 30% solids and containing the benzotriazole-diol of Example 1 and succinic anhydride in a tool ratio of 4:5.

On drying, the polymer forms a hard, clear, light brown film. The molecular weight, as determined by titration of carboxylic end groups, is 3850.

EXAMPLE 23

The polyester product of Example 22 is emulsified according to Example 17 and spray-applied to the surface of brown aniline leather to give an add-on of 1.17g actives/ft². The sprayed leather is subsequently dried at 70° C. for ten minutes, put into exposure frames and then subjected to UV radiation in an Arias xenon arc WEATHER-O-METER controlled irradiation exposure system for 48 hours. Excellent resistance to fading is observed.

What is claimed is:

1. A polyurethane of 1,000 to 15,000 molecular weight of the formula I

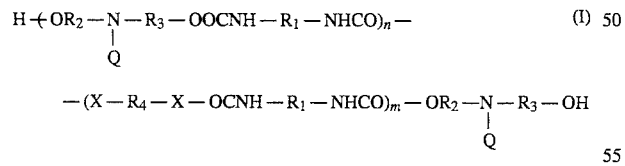

wherein n is a number from 2 to 20, m is zero to 5, $R_1$ is the diradical residue of an aliphatic, cycloaliphatic or aromatic diisocyanate with structure OCN-$R_1$-NCO, $R_2$ and $R_3$ independently of each other are $C_2$-$C_6$alkylene, $R_4$ is the diradical residue of a diol or diamine of 40 to 5000 molecular weight, X is oxygen or -NH- and Q is a radical of the formula

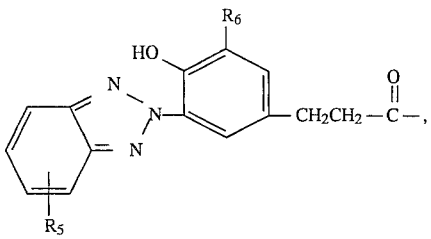

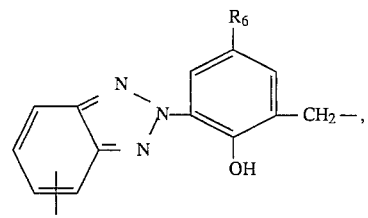

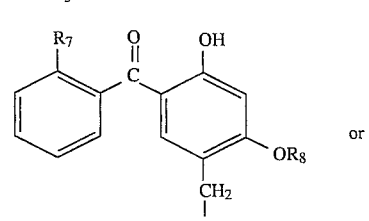

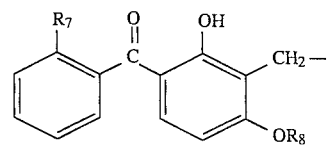

in which $R_5$ is hydrogen, chlorine or $C_1$-$C_4$alkyl, $R_6$ is $C_1$-$C_8$alkyl, $R_7$ is hydrogen or hydroxyl and $R_8$ is hydrogen or $C_1$-$C_8$alkyl, with the proviso that the sum of m+n is such that the resulting polymer has an average molecular weight of 1,000 to 15,000.

2. A polyurethane of the formula I according to claim 1, wherein $R_1$ is the diradical residue of a diisocyanate of structure OCN-$R_1$-NCO selected from the group consisting of 1-isocyanatomethyl-5-isocyanato- 1,3,3-trimethylcyclohexane, hexane- 1,6-diisocyanate, 2,2,4-(2,4,4)-trimethylhexane- 1,6-diisocyanate, bis-(4-isocyanatocyclohexenyl-)methane, ethylene diisocyanate, 1,2-diisocyanatopropane, 3-diisocyanatopropane, 1,2-diisocyanato-cyclohexane, 1,3-diisocyanatocyclohexane, 1,4-diisocyanatobenzene, bis(4-isocyanatocyclohexyl)methane, bis(4-isocyanatophenyl-)methane, 2,6- and 2,4-toluene diisocyanate, 3,3-dichloro-4,4'-diisocyanatobiphenyl, tris(4-isocyanatophenyl)methane, 1,5-diisocyanato-naphthalene, hydrogenated toluene diisocyanate, 1,3,5-tris(6-isocyanato-hexyl)biuret, 2,2'-diisocyanatodiethyl fumarate, 1,5-diisocyanato-1-carboxypentane, 1,2-, 1,3-, 1,6-, 1,7-, 1,8-, 2,7- and 2,3-diisocyanatonaphthalene, 2,4- and 2,7-diisocyanato-1-methylnaphthalene, 4,4'-diisocyanatobiphenyl, 4,4'-diisocyanato-3,3'-diisocyanato- 6(7)-methylnaphthalene; 4,4'-diisocyanato-2,2'-dimethyl biphenyl, bis-(4-isocyanatophenyl)ethane and bis(4-isocyanatophenyl) ether.

3. A polyurethane of the formula I according to claim 2, wherein m is zero.

4. A polyurethane of the formula I according to claim 3, wherein n is 2 to 10, $R_1$ is the diradical residue of a diisocyanate of structure $OCN-R_1-NCO$ selected from the group consisting of 1-isocyanatomethyl-5-isocyanato-1,3,3-trimethylcyclohexane, hexane-1,6-diisocyanate, 2,2,4-(2,4,4)-trimethylhexane-1,6-diisocyanate and bis-(4-isocyanatocyclohexenyl)methane, $R_2$ and $R_3$ are ethylene, Q is $Q_1$, $R_5$ is hydrogen and $R_6$ is tertiary butyl.

5. A polyurethane of the formula I according to claim 3, wherein n is 2 to 10, $R_1$ is the diradical residue of a diisocyanate of structure $OCN-R_1-NCO$ selected from the group consisting of 1-isocyanatomethyl-5-isocyanato-1,3,3-trimethylcyclohexane, hexane-1,6-diisocyanate, 2,2,4-(2,4,4)-trimethylhexane-1,6-diisocyanate and bis-(4-isocyanatocyclohexenyl)methane, $R_2$ and $R_3$ are ethylene, Q is $Q_2$, $R_5$ is hydrogen and $R_6$ is tertiary butyl.

6. A polyurethane of the formula I according to claim 3, wherein n is 2 to 10, $R_1$ is the diradical residue of a diisocyanate of structure $OCN-R_1-NCO$ selected from the group consisting of 1-isocyanatomethyl-5-isocyanato-1,3,3-trimethylcyclohexane, hexane-1,6-diisocyanate, 2,2,4-(2,4,4)-trimethylhexane-1,6-diisocyanate and bis-(4-isocyanatocyclohexenyl)methane, $R_2$ and $R_3$ are ethylene, Q is $Q_3$ or $Q_4$, $R_7$ is hydrogen and $R_8$ is methyl.

7. A polyurethane of the formula I according to claim 3, wherein m is 1 or more and $R_4$ is the diradical residue of a poly-($C_2$-$C_4$alkyleneoxide), a poly-(dimethylsiloxane)-$\alpha,\omega$-dialkylene of 500 to 3000 molecular weight or a tertiary nitrogen-containing diol residue of 40 to 500 molecular weight.

8. A polyurethane of the formula I according to claim 7, wherein n is 2 to 5, $R_1$ is the diradical residue of a diisocyanate of structure $OCN-R_1-NCO$ selected from the group consisting of 1-isocyanatomethyl-5-isocyanato-1,3,3-trimethylcyclohexane, hexane-1,6-diisocyanate, 2,2,4-(2,4,4)-trimethylhexane-1,6-diisocyanate and bis-(4-isocyanatocyclohexenyl)methane, $R_2$ and $R_3$ are ethylene, Q is $Q_1$, $R_4$ is a poly-(tetramethyleneoxide) or a tertiary nitrogen-containing diol residue of 40 to 500 molecular weight, $R_5$ is hydrogen and $R_6$ is tert-butyl.

9. A polyurethane of the formula I according to claim 7, wherein n is 2 to 5, $R_1$ is the diradical residue of a diisocyanate of structure $OCN-R_1-NCO$ selected from the group consisting of 1-isocyanatomethyl-5-isocyanato-1,3,3-trimethylcyclohexane, hexane-1,6-diisocyanate, 2,2,4-(2,4,4)-trimethylhexane-1,6-diisocyanate and bis-(4-isocyanatocyclohexenyl)methane, $R_2$ and $R_3$ are ethylene, Q is $Q_2$, $R_4$ is a poly-(tetramethyleneoxide) or a tertiary nitrogen-containing diol residue of 40 to 500 molecular weight, $R_5$ is hydrogen and $R_6$ is ten-butyl.

10. A polyurethane of the formula I according to claim 7, wherein n is 2 to 5, $R_1$ is the diradical residue of a diisocyanate of structure $OCN-R_1-NCO$ selected from the group consisting of 1-isocyanatomethyl-5-isocyanato-1,3,3-trimethylcyclohexane, hexane-1,6-diisocyanate, 2,2,4-(2,4,4)-trimethylhexane-1,6-diisocyanate and bis-(4-isocyanatocyclohexenyl)methane, $R_2$ and $R_3$ are ethylene, Q is $Q_3$ or $Q_4$, $R_4$ is a poly-(tetramethyleneoxide) or a tertiary nitrogen-containing diol residue of 40 to 500 molecular weight, $R_7$ is hydrogen and $R_8$ is methyl.

11. A composition for protecting a substrate from degradation by UV radiation, which comprises a polyurethane of the formula I according to claim 1 dissolved or suspended in a liquid.

12. A method of protecting a substrate from degradation by UV radiation, which comprises applying to at least one surface of said substrate a composition according to claim 11.

13. A method according to claim 12, wherein the substrate is leather, paper, raw wood or a textile material.

* * * * *